US011648329B1

(12) United States Patent
Chan et al.

(10) Patent No.: US 11,648,329 B1
(45) Date of Patent: May 16, 2023

(54) AIR PURIFIERS

(71) Applicant: RHT Limited, Hong Kong (CN)

(72) Inventors: Chi Keung Rudy Chan, Hong Kong (CN); Ka Wai Jim, Hong Kong (CN); Lam Lung Yeung, Hong Kong (CN)

(73) Assignee: RHT LIMITED, Hong Kong (CN)

( * ) Notice: Subject to any disclaimer, the term of this patent is extended or adjusted under 35 U.S.C. 154(b) by 0 days.

(21) Appl. No.: 17/535,569

(22) Filed: Nov. 24, 2021

(51) Int. Cl.
*A61L 9/015* (2006.01)
*B01J 23/34* (2006.01)
(Continued)

(52) U.S. Cl.
CPC ............. *A61L 9/015* (2013.01); *A61L 2/022* (2013.01); *A61L 9/122* (2013.01); *B01D 46/0028* (2013.01); *B01D 46/0049* (2013.01); *B01D 53/8675* (2013.01); *B01J 20/18* (2013.01); *B01J 21/04* (2013.01); *B01J 21/08* (2013.01); *B01J 23/34* (2013.01); *B01J 29/061* (2013.01); *B01J 35/023* (2013.01); *B01J 35/026* (2013.01); *B01J 35/1057* (2013.01); *B01J 35/1061* (2013.01); *F24F 8/108* (2021.01); *F24F 8/167* (2021.01); *F24F 8/26* (2021.01); *A61L 2209/11* (2013.01); *A61L 2209/14* (2013.01); *A61L 2209/212* (2013.01); *B01D 2255/2073* (2013.01);
(Continued)

(58) Field of Classification Search
CPC .................. A61L 9/015; B01J 23/34
See application file for complete search history.

(56) References Cited

U.S. PATENT DOCUMENTS

| 4,244,937 A | 1/1981 | Durkin |
| 4,673,416 A | 6/1987 | Sakakibara et al. |

(Continued)

FOREIGN PATENT DOCUMENTS

| CN | 2317432 Y | 5/1999 |
| CN | 1275436 A | 12/2000 |

(Continued)

OTHER PUBLICATIONS

Sen SE, Smith SM, Sullivan KA. Organic transformations using zeolites and zeotype materials Tetrahedron. Oct. 29, 1999;55(44):12657-98.

(Continued)

*Primary Examiner* — Kevin Joyner
(74) *Attorney, Agent, or Firm* — Eagle IP Limited (57) ABSTRACT

In certain exemplary embodiments, an air purifier comprises a housing defining an enclosure and having an air entrance and an air exit; a particulate filter; a NCCO filter material configured to adsorb and decompose at least one gaseous pollutant; an AOG configured to generate at least one oxidant; an oxidant remover configured to remove at least one oxidant; a fan unit configured to generate airflow from the air entrance to the air exit; wherein the particulate filter, the NCCO filter material, the AOG, the oxidant remover and the fan unit are positioned within the enclosure such that during operation, a flow of air passes from the air entrance to the air exit through the particulate filter and the NCCO filter material along a direction of the flow of air. In certain embodiments, the air purifier may ensure safety to users while efficiency in removing contaminants can be greatly improved.

30 Claims, 4 Drawing Sheets

(51) Int. Cl.
*B01J 21/04* (2006.01)
*B01J 21/08* (2006.01)
*B01J 29/06* (2006.01)
*B01J 35/02* (2006.01)
*B01J 35/10* (2006.01)
*F24F 8/26* (2021.01)
*F24F 8/108* (2021.01)
*F24F 8/167* (2021.01)
*B01D 53/86* (2006.01)
*B01D 46/00* (2022.01)
*A61L 9/12* (2006.01)
*A61L 2/02* (2006.01)
*B01J 20/18* (2006.01)

(52) U.S. Cl.
CPC .. *B01D 2255/2092* (2013.01); *B01D 2255/30* (2013.01); *B01D 2255/50* (2013.01); *B01D 2255/9202* (2013.01); *B01D 2257/106* (2013.01); *B01D 2273/30* (2013.01); *B01D 2279/65* (2013.01)

(56) References Cited

U.S. PATENT DOCUMENTS

| | | | |
|---|---|---|---|
| 4,772,297 A | 9/1988 | Anzai | |
| 4,780,277 A | 10/1988 | Tanaka et al. | |
| 4,872,083 A | 10/1989 | Blitshteyn | |
| 5,141,906 A | 8/1992 | Takeshima et al. | |
| 5,186,903 A * | 2/1993 | Cornwell | A61L 9/16 422/4 |
| 5,221,520 A | 6/1993 | Cornwell | |
| 5,388,177 A | 2/1995 | Ono et al. | |
| 5,622,630 A | 4/1997 | Romano | |
| 5,685,895 A | 11/1997 | Hagiwara et al. | |
| 5,702,507 A | 12/1997 | Wang | |
| 5,835,840 A | 11/1998 | Goswami | |
| 5,843,288 A | 12/1998 | Yamamoto | |
| 5,885,546 A | 3/1999 | Kumar et al. | |
| 5,939,028 A | 8/1999 | Bennett et al. | |
| 5,961,919 A | 10/1999 | Tachibana et al. | |
| 6,120,584 A | 9/2000 | Sakata et al. | |
| 6,152,996 A | 11/2000 | Linnersten et al. | |
| 6,162,996 A | 12/2000 | Schmidt et al. | |
| 6,299,854 B1 | 10/2001 | Henmi et al. | |
| 6,358,374 B1 | 3/2002 | Obee et al. | |
| 6,489,259 B2 | 12/2002 | LaBarge et al. | |
| 6,607,702 B1 | 8/2003 | Kang et al. | |
| 6,887,438 B2 | 5/2005 | Labarge et al. | |
| 2002/0014071 A1 | 2/2002 | Balmer et al. | |
| 2002/0157661 A1 | 10/2002 | Kornberger | |
| 2003/0030374 A1 | 2/2003 | Pai | |
| 2005/0215420 A1 * | 9/2005 | Collier | A61L 9/014 502/64 |
| 2011/0224066 A1 * | 9/2011 | Schmidt | B01J 35/004 502/100 |
| 2012/0132851 A1 * | 5/2012 | Blanchard | D04H 3/004 264/211 |
| 2014/0037522 A1 * | 2/2014 | Hauville | B01D 53/90 423/210 |
| 2018/0117522 A1 | 5/2018 | Gaur | |
| 2020/0340680 A1 * | 10/2020 | Kang | B01D 46/0036 |
| 2021/0331937 A1 * | 10/2021 | DuBois | C01G 45/1264 |

FOREIGN PATENT DOCUMENTS

| | | |
|---|---|---|
| CN | 1340679 A | 3/2002 |
| CN | 102548636 A | 7/2012 |
| CN | 104913394 A | 9/2015 |
| CN | 105107524 A | 12/2015 |
| CN | 107537473 A | 1/2018 |
| CN | 108613260 A | 10/2018 |
| CN | 109759054 A | 5/2019 |
| CN | 111266137 A | 6/2020 |
| EP | 0616175 A2 | 9/1994 |
| EP | 0950800 A2 | 10/1999 |
| EP | 1905458 A2 | 4/2008 |
| JP | S54104481 A | 8/1979 |
| JP | H06327922 A | 11/1994 |
| JP | H11137658 A | 5/1999 |
| JP | H11221442 A | 8/1999 |
| JP | 2001246227 A | 9/2001 |
| RU | 1623346 A3 | 5/1998 |
| RU | 2747863 C1 | 5/2021 |
| TW | 587146 B | 5/2004 |

OTHER PUBLICATIONS

Thomas JM, Raja R, Sankar G, Bell RG. Molecular-sieve catalysts for the selective oxidation of linear alkanes by molecular oxygen. Nature. Mar. 1999;398(6724):227-30.

Eliasson B, Kogelschatz U. Nonequilibrium volume plasma chemical processing. IEEE transactions on plasma science. Dec. 1991;19(6):1063-77.

Liu CJ, Vissokov GP, Jang BW. Catalyst preparation using plasma technologies. Catalysis Today. Mar. 15, 2002,72 (3-4):173-84.

Francke KP, Miessner H, Rudolph R. Plasmacatalytic processes for environmental problems. Catalysis Today. Jun. 25, 2000;59(3-4):411-6.

Leichsenring S, Lenoir D, May HG, Kettrup A. Catalytic oxidation of chloromatic trace contaminations adsorbed on Wessalith DAY by ozone. Chemosphere. Jul. 1, 1996;33(2):343-52.

Oda T, Kato T, Takahashi T, Shimizu K. Nitric oxide decomposition in air by using nonthermal plasma processing with additives and catalyst. IEEE Transactions on Industry Applications. Mar. 1998;34(2):268-72.

Yan K, Hui H, Cui M, Miao J, Wu X, Bao C, Li R. Corona induced non-thermal plasmas: fundamental study and industrial applications. Journal of electrostatics. Jul. 1, 1998;44(1-2):17-39.

Urashima K, Kostov KG, Chang JS, Okayasa Y, Iwaizumi T, Yoshimura K, Kato T. Removal of C/sub 2/F/sub 6/from a semiconductor process flue gas by a ferroelectric packed-bed barrier discharge reactor with an adsorber. IEEE Transactions on Industry Applications. Sep. 2001;37(5):1456-63.

Francke KP, Miessner H, Rudolph R. Cleaning of air streams from organic pollutants by plasma-catalytic oxidation. Plasma Chemistry and Plasma Processing Sep. 2000;20(3):393-403.

Weitkamp J. Zeolites and catalysis. Solid state ionics. Jun. 1, 2000;131(1-2):175-88.

Zhu B, Li XS, Sun P, Liu JL, Ma XY, Zhu X, Zhu AM. A novel process of ozone catalytic oxidation for low concentration formaldehyde removal Chinese Journal of Catalysis. Oct. 1, 2017;38(10):1759-69.

Zhang Y, Shi J, Fang W, Chen M, Zhang Z, Jiang Z, Shangguan W, Einaga H. Simultaneous catalytic elimination of formaldehyde and ozone over one-dimensional rod-like manganese dioxide at ambient temperature. Journal of Chemical Technology & Biotechnology. Jul. 2019;94(7):2305-17.

Fang R, Huang W, Huang H, Feng Q, He M, Ji J, Liu B, Leung DY. Efficient MnOx/SiO2@ AC catalyst for ozone-catalytic oxidation of gaseous benzene at ambient temperature Applied Surface Science. Mar. 15, 2019;470:439-47.

* cited by examiner

AIR PURIFIERS

FIELD OF INVENTION

This invention relates to ventilation devices, and in particular relates to air purifiers.

BACKGROUND OF INVENTION

Poor air quality can lead to the irritation of eyes, nose and throat and exacerbate asthma, allergy and other respiratory or cardiovascular conditions. To improve air quality, air purifiers are used to remove various contaminants/pollutants from the air. These devices can also prevent airborne diseases by removing and/or killing microbes such as bacteria, viruses, mold and/or fungal spores from the air. However, the contaminants/pollutants, bacteria and viruses are continuously accumulated onto the filter medium of the air purifiers, thus the filters have to be cleaned or replaced periodically. Since the accumulated contaminants/pollutants, bacteria and viruses still remain onto the filter medium after air filtration, the cleaning processes of the filters can be hazardous and chaotic. Some air purifiers may leak harmful gaseous by-products that are risky to human health. An improved air purifier is highly desired.

SUMMARY OF INVENTION

In light of the foregoing background, in certain embodiments, it is an object to provide an improved air purifier.

Accordingly, in one aspect, an exemplary embodiment of the present disclosure is to provide an air purifier, comprising a housing, a particulate filter, a nano-confined catalytic oxidation (NCCO) filter material, an active oxygen generator (AOG), an oxidant remover material and a fan unit. The housing defines an enclosure and has an air entrance and an air exit. The NCCO filter material is configured to adsorb and decompose at least one gaseous pollutant. The AOG is configured to generate at least one oxidant. The oxidant remover material is configured to remove at least one oxidant. The fan unit is configured to generate airflow from the air entrance to the air exit. The particulate filter, the NCCO filter material, the AOG, the oxidant remover material and the fan unit are positioned within the enclosure such that during operation, a flow of air passes from the air entrance to the air exit through the particulate filter and the NCCO filter material along a direction of the flow of air.

In another aspect, provided is a self-regenerating air purifier for air disinfection, comprising a housing, a high-efficiency particulate air (HEPA) filter, a NCCO filter material, an ozone generator, an ozone remover material, a fan unit and a pre-filter. The housing defines an enclosure and has an air entrance and an air exit. The NCCO filter material is configured to adsorb and decompose at least one gaseous pollutant. The ozone generator is configured to generate ozone. The ozone remover material is configured to remove ozone, comprising a catalyst composition comprising a porous material and manganese oxides. The porous material has a plurality of nanopores and comprises one or more of silicon dioxide, aluminum oxide, and zeolite, and the manganese oxides comprise manganese in an amount of about 0.1-50% by weight of the total catalyst composition. The fan unit is configured to generate airflow from the air entrance to the air exit. The pre-filter is positioned to cover at least a portion of the air entrance and/or the air exit to filter air passing through the air entrance and/or the air exit. The HEPA filter, the NCCO filter material, the ozone generator, the ozone remover material and the fan unit are positioned within the enclosure such that a flow of air passes from the air entrance to the air exit through the HEPA filter and the NCCO filter material. The ozone generator is configured to generate a concentration of ozone sufficient to disinfect at least 90% of bacteria/viruses.

Advantages of the Current Invention

There are various advantages in the various embodiments of the present disclosure. For example, in certain embodiments, the improved air purifiers and systems thereof contain an AOG that can achieve disinfection inside the system and contains certain novel oxidant remover materials or catalyst compositions which can act as an oxidant guard to ensure that no excessive oxidant from the AOG will be released into the environment. In certain embodiments, the AOG generates ozone as the oxidant and the oxidant remover materials act as an ozone guard. As such, oxidant generation by the AOG of the air purifiers can be further increased or optimized in order to enhance the efficiency of degradation of contaminants/pollutants and/or microbes such as bacteria and viruses, while preventing excessive oxidant such as ozone being released into the environment. Therefore, safety to users and efficiency in removing contaminants can greatly improved at the same time.

Additionally, in certain embodiments, the disclosed catalyst compositions provide a high quality of the manganese-doped porous materials, and thus enhances the oxidant removal efficiency of the catalyst composition compared to the previously-known compositions. Moreover, in certain embodiments, the gaseous pollutant with the oxidant is adsorbed into the cavities of a porous material, such as zeolite, and therefore the porous material secures the adsorbed contaminant and oxidant into a confined space, which leads to improving the efficiency of decomposing the contaminant by means of oxidation.

Other exemplary embodiments are discussed herein.

DETAILED DESCRIPTION

As used herein and in the claims, the terms "comprising" (or any related form such as "comprise" and "comprises"), "including" (or any related forms such as "include" or "includes"), "containing" (or any related forms such as "contain" or "contains"), means including the following elements but not excluding others. It shall be understood that for every embodiment in which the term "comprising" (or any related form such as "comprise" and "comprises"), "including" (or any related forms such as "include" or "includes"), or "containing" (or any related forms such as "contain" or "contains") are used, this disclosure/application also includes alternate embodiments where the term "comprising," "including," or "containing," is replaced with "consisting essentially of" or "consisting of." These alternate embodiments that use "consisting of" or "consisting essentially of" are understood to be narrower embodiments of the "comprising," "including," or "containing" embodiments.

For example, alternate embodiments of "a composition comprising A, B, and C" would be "a composition consisting of A, B, and C" and "a composition consisting essentially of A, B, and C." Even if the latter two embodiments are not explicitly written out, this disclosure/application includes those embodiments. Furthermore, it shall be understood that the scopes of the three embodiments listed above are different.

For the sake of clarity, "comprising," including, and "containing," and any related forms are open-ended terms which allow for additional elements or features beyond the named essential elements, whereas "consisting of" is a closed-end term that is limited to the elements recited in the claim and excludes any element, step, or ingredient not specified in the claim.

As used herein, the singular forms "a," "an" and "the" are intended to include the plural forms as well, unless the context clearly indicates otherwise. Where a range is referred to in the specification, the range is understood to include each discrete point within the range. For example, 1-7 means 1, 2, 3, 4, 5, 6, and 7.

As used herein, "Nano Confined Catalytic Oxidation (NCCO)" refers to the technology in which active oxygens are emitted from a generator and kill bacteria and viruses, as well as destroy the molecular structure of harmful chemicals. As an example, NCCO filter material may be zeolite having pore size in the range of 4 Angstroms to 20 Angstroms.

As used herein, "active oxygen generator (AOG)" refers to a device that generates at least one type of oxidants. In certain embodiments, one type of oxidants is ozone.

As used herein, "high-efficiency particulate air (HEPA) filter" refers to an air filter that meets a HEPA efficiency standard. Common HEPA standards requires that a HEPA air filter must remove at least 99.95% (ISO, European Standard) or 99.97% (ASME, U.S. DOE) of particles whose diameter is equal to 0.3 µm, with the filtration efficiency increasing for particle diameters both less than and greater than 0.3 µm.

As used herein "ultra-low particulate air (ULPA) filter" refers to an air filter that requires a standard of removing 99.9995% of particles (dust, pollen, mold, bacteria and any airborne particles) down to 1.2 µm from the air. In certain embodiments, the denser media of the ULPA filter reduces airflow 20% to 50% for filters of the same dimensions.

As used herein, "zeolite" refers to microporous, aluminosilicate minerals commonly used as commercial adsorbents and catalysts.

As used herein, "deposition" refers to depositing a particular material onto the surface of another material. In certain embodiments, it refers to depositing manganese oxides on porous materials.

As used herein, "doping" refers to the introduction of impurities into material for the purpose of modulating its properties. In some embodiments, doping refers to adding small amounts of manganese oxides into porous materials.

As used herein, "ion exchange" refers to a reversible interchange of one kind of ion present on an insoluble solid with another of similarly charged ion present in a solution surrounding the solid.

As used herein, "overnight" refers to a few hours that cover the duration of a night. In some embodiments, this is 5-24 hours, 5-18 hours, or 5-12 hours.

As used herein, "calcination" refers to a process of heating of solids to high temperature for the purpose of removing volatile substances, oxidizing a portion of the mass, or rendering them friable.

Although the description referred to particular embodiments, the disclosure should not be construed as limited to the embodiments set forth herein.

Air Purifiers

In certain exemplary embodiments, an air purifier comprises a housing defining an enclosure and having an air entrance and an air exit; a particulate filter; a NCCO filter material configured to adsorb and decompose at least one gaseous pollutant; an AOG configured to generate at least one oxidant; an oxidant remover material configured to remove at least one oxidant; a fan unit configured to generate airflow from the air entrance to the air exit; wherein the particulate filter, the NCCO filter material, the AOG, the oxidant remover and the fan unit are positioned within the enclosure such that during operation, a flow of air passes from the air entrance to the air exit through the particulate filter and the NCCO filter material along a direction of the flow of air.

In some embodiments, the AOG is an ozone generator and the at least one oxidant is ozone. In some embodiments, the oxidant remover is an ozone remover material. In some embodiments, the particulate filter is a HEPA filter.

In some embodiments, the particulate filter is an Ultra-low Penetration Air (ULPA) filter. In some embodiments, the ULPA filter is used for medical laboratories, removing particulates from cleanrooms, or filtering toxic surgical plumes emitted during electro-surgical operations.

In some embodiments, the ozone remover material comprises a catalyst composition comprising: a porous material having a plurality of nanopores and comprising one or more of silicon dioxide, aluminum oxide, and zeolite; and manganese oxides comprising manganese in an amount of about 0.1-50% by weight of the total catalyst composition.

Example 1

Figure 1:
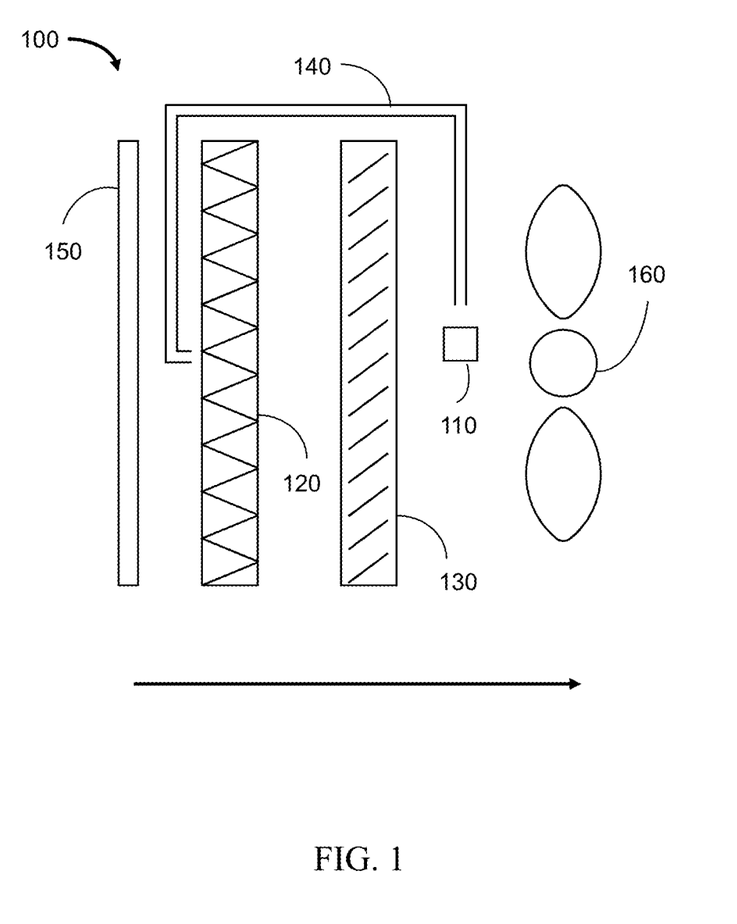
FIG. 1 is a schematic diagram which illustrates an example embodiment of NCCO design.

FIG. 1 shows one example embodiment of an example air purifier 100. The air purifier 100 generally includes a pre-filter 150, a particulate filter 120, a catalyst layer 130 which contains nano-confined catalytic oxidation (NCCO) filter material and oxidant remover material, an active oxygen generator (AOG) 110, an air channel 140, and a fan unit 160. In certain embodiments, the air purifier 100 may further include a housing (not shown) defining an enclosure and having an air entrance and an air exit. For the ease of description, the side allowing air entrance is called front side and the opposite side allowing air exit is called back side. The pre-filter 150 is optional for filtering larger particulates from air, e.g., dusk and is disposed in the front of the air purifier 100. The particular filter 120 may be arranged behind the pre-filter 150 and may include one or more of HEPA filters and ULPA filters. The catalyst layer 130 may include a mixture of the NCCO filter material and the oxidant remover material. As an example, the catalyst layer 130 may have a thickness of about 5-20 mm. As an example, the NCCO filter material and the oxidant remover material may be arranged substantially in two discrete layers. For example, the NCCO filter material may be substantially arranged at the front side of catalyst layer 130 while the oxidant remover material may be substantially arranged at the back side of catalyst layer 130, and vice versa. As an example, the NCCO filter material and the oxidant remover material may be porous materials in the form of granules. As an example, the NCCO filter material and the oxidant remover material may be mixed together to form a non-discrete catalyst layer 130. Various ratios between the NCCO filter material and the oxidant remover material may be used, depending on the practical need. As an example, the ratio between NCCO filter material and the oxidant remover material is 1:100, 1:50, 1:10, 1:5, 1:3, 1:1 or even more. As an example, the ratio between NCCO filter material and the oxidant remover material is 2:1, 3:1, 5:1, 10:1, 50:1, 100:1 or even less. In some other embodiments, the catalyst layer 130 may only include the oxidant remover material but may not comprise the NCCO filter material. The AOG 110 is disposed between the catalyst layer 130 and the fan unit 150, and is configured to generate at least one oxidant and is in gas communication with the particulate filter 120 via the air channel 140. As an example, the AOG 110 is an ozone generator to generate ozone. The fan unit 160 is arranged to generate an air flow through the air purifier 100. An air flow from the air entrance to the air exit is driven by the fan unit 160, as indicated by the arrow.

During operation, a flow of air substantially passes from the air entrance to the air exit through the particulate filter and the NCCO filter material along a direction of the flow of air. The air from air entrance is configured to pass through the pre-filter 150 first, driven by the fan unit 160. Then, the pre-filtered air is configured to pass through the particulate filter 120 to filter finer particles, certain contaminants/pollutants including microbes (such as bacteria and viruses). Subsequently, the air passes through the catalyst layer 130 to remove gaseous contaminants by the NCCO filter material. The filtered air is then mixed with one or more oxidants generated by the AOG 110. Any excessive oxidant(s) from the AOG 110 may be absorbed and decomposed by the oxidant remover material in the catalyst layer 130. As such, no excessive oxidant will be leaked out from the air purifier 100, improving the safety to users. The oxidant release rate of the AOG 110 may be greatly increased to improve the efficiency without the risk of releasing excessive oxidants to the environment. As an example, the AOG may be configured at 6 kV or above. As an example, the AOG may be configured to release at least 40 ppb of ozone. At the same time, oxidants generated by the AOG 110 may be also delivered in front of the particular filter 120 through the air channel 140 to decontaminate/decompose the contaminants accumulated on the filter, thereby continuously regenerating the particulate filter 120. As such, the particulate filter 120 has a prolonged working life. Cleaned air may eventually pass through by air exit.

In certain embodiments, the NCCO filter material includes porous material such as zeolite. As an example, the zeolite may have a pore size in the range of 4 Angstroms to 20 Angstroms. In certain embodiments, the zeolite includes hydrophilic zeolite and/or hydrophobic zeolite.

Example 2

Figure 2:
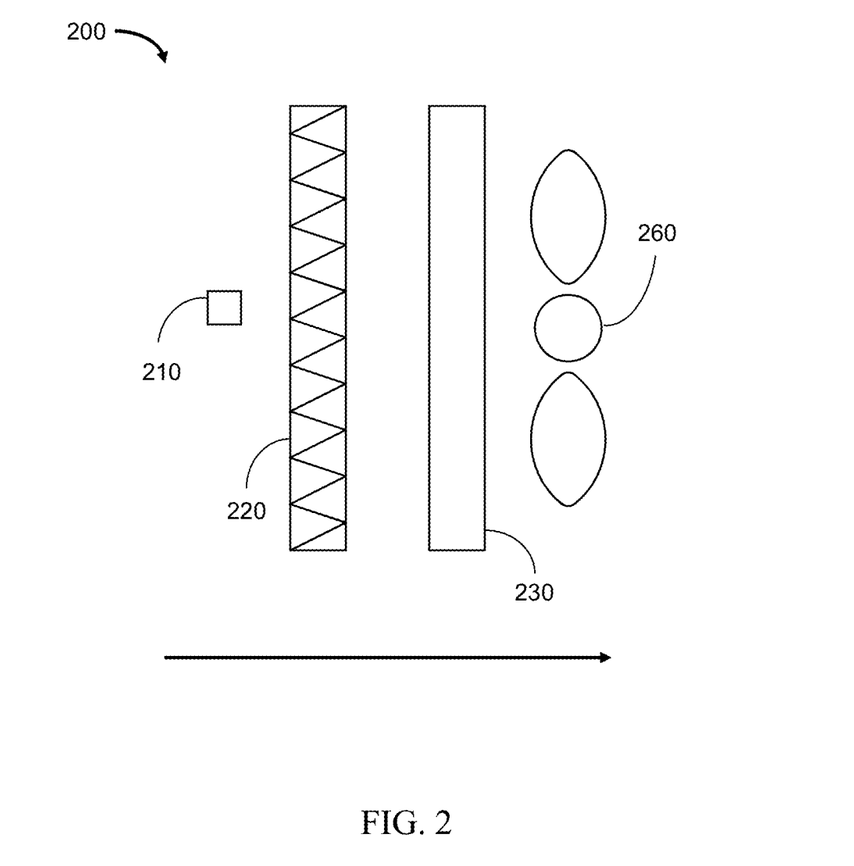
FIG. 2 is a schematic diagram which illustrates another example embodiment of NCCO design.

FIG. 2 is a schematic diagram that illustrate another example embodiment of an example air purifier 200. The air purifier 200 includes a particulate filter 220, a catalyst layer 230 which contains NCCO filter material and oxidant remover material, an AOG 210, and a fan unit 260. In certain embodiments, the air purifier 200 may also include a housing (not shown) defining an enclosure and having an air entrance and an air exit. In this example, the AOG 210 is positioned at the front side of the air purifier 200. The particulate filter 220 may be arranged behind the AOG 210 and may include one or more of HEPA filters and/or ULPA filters. The catalyst layer 230 may include a mixture of the NCCO filter material and the oxidant remover material. As an example, the catalyst layer 230 may have a thickness of about 5-20 mm. As an example, the NCCO filter material and the oxidant remover material may be arranged substantially in two discrete layers in the catalyst layer 230. For example, the NCCO filter material may be substantially arranged at the back side of catalyst layer 230 while the oxidant remover material may be substantially arranged at the front side of catalyst layer 230 facing the particulate filter 220, and vice versa. As an example, the NCCO filter material and the oxidant remover material may comprise porous materials in the form of granules. As an example, the NCCO filter material and the oxidant remover material may be mixed together to form a non-discrete catalyst layer 230. Various ratios between the NCCO filter material and the oxidant remover material may be used, depending on the practical need. As an example, the ratio between NCCO filter material and the oxidant remover material is 1:100, 1:50, 1:10, 1:5, 1:3, 1:1 or even more. As an example, the ratio between NCCO filter material and the oxidant remover material is 2:1, 3:1, 5:1, 10:1, 50:1, 100:1 or even less. In some other embodiments, the catalyst layer 130 may only include the oxidant remover material but may not comprise the NCCO filter material. The AOG 210 is disposed before the particulate filter 220, and is configured to generate at least one oxidant. As an example, the AOG 210 is an ozone generator to generate ozone. The fan unit 260 is arranged to generate an air flow through the air purifier 200. An air flow from the air entrance to the air exit is driven by the fan unit 260.

During operation of the air purifier 200, a flow of air substantially passes from the air entrance to the air exit through the particulate filter 220 and the catalyst layer 230 along a direction of the flow of air, as indicated by the arrow. The air from the air entrance may be in contact with one or more oxidants generated by the AOG 210, so that the gaseous pollutants may be decomposed and/or microbes may be killed by the oxidants. The air passes through the particulate filter 220 to filter particles, certain contaminants/pollutants including microbes (such as bacteria and viruses). The oxidants generated by the AOG 110 may at the same time decontaminate/decompose the contaminants accumulated on the filter, thereby continuously regenerating particulate filter 220. Any excessive oxidant(s) from the AOG 210 may be absorbed and decomposed by the oxidant remover material in the catalyst layer 230 disposed at the back of the particulate filter 220. As such, no excessive oxidant will be leaked out from the air purifier 200 to the environment, improving the safety to users. Subsequently, the air passes through the catalyst layer 230 to remove gaseous contaminants by the NCCO filter material. Any excessive oxidant(s) from the AOG 210 may be absorbed and decomposed by the oxidant remover material in the composite layer 230. As such, no excessive oxidant will be leaked out from the air purifier 200, improving the safety to users. In this example, the air purifier 200 does not include a pre-filter.

In some embodiments, oxidants include ozone, oxygen, hydrogen peroxide and other inorganic peroxides, Fenton's reagent, fluorine, chlorine, and other halogens, nitric acid and nitrate compounds, sulfuric acid, peroxydisulfuric acid, peroxymonosulfuric acid, hypochlorite, chlorite, chlorate, perchlorate, and other analogous halogen compounds like household bleach (NaClO), hexavalent chromium compounds such as chromic and dichromic acids and chromium trioxide, pyridinium chlorochromate, and chromate/dichromate compounds, permanganate compounds such as potassium permanganate, sodium perborate, nitrous oxide, nitrogen dioxide/dinitrogen tetroxide, potassium nitrate, the oxidizer in black powder, sodium bismuthate, cerium compounds such as ceric ammonium nitrate and ceric sulfate, sodium dichromate.

In some embodiments, the AOG is configured to generate a concentration of ozone sufficient to disinfect at least 90% of bacteria/viruses. In some embodiments, the AOG is configured to generate an ozone release rate of at least 10-2000 ppb within 0-5 minutes. In some embodiments, the ozone release rate is at least 40 ppb over 1 minute. In some embodiments, the AOG is configured to release a total concentration of 40 ppb of ozone.

In certain embodiments, the AOG is configured to generate an ozone release rate of at least 10-50 ppb within 0-5 minutes, 50-100 ppb within 0-5 minutes, 100-150 ppb within 0-5 minutes, 150-200 ppb within 0-5 minutes, 200-250 ppb within 0-5 minutes, 250-300 ppb within 0-5 minutes, 300-350 ppb within 0-5 minutes, 350-400 ppb within 0-5 minutes, 400-450 ppb within 0-5 minutes, 450-500 ppb within 0-5 minutes, 500-550 ppb within 0-5 minutes, 550-600 ppb within 0-5 minutes, 600-650 ppb within 0-5 minutes, 650-700 ppb within 0-5 minutes, 700-750 ppb within 0-5 minutes 750-800 ppb within 0-5 minutes, 800-850 ppb within 0-5 minutes, 850-900 ppb within 0-5 minutes, 900-950 ppb within 0-5 minutes, 950-1000 ppb within 0-5 minutes, 1000-1050 ppb within 0-5 minutes, 1050-1100 ppb within 0-5 minutes, 1100-1150 ppb within 0-5 minutes, 1150-1200 ppb within 0-5 minutes, 1200-1250 ppb within 0-5 minutes, 1250-1300 ppb within 0-5 minutes, 1300-1350 ppb within 0-5 minutes, 1350-1400 ppb within 0-5 minutes, 1400-1450 ppb within 0-5 minutes, 1450-1500 ppb within 0-5 minutes, 1500-1550 ppb within 0-5 minutes, 1550-1600 ppb within 0-5 minutes, 1600-1650 ppb within 0-5 minutes, 1650-1700 ppb within 0-5 minutes, 1700-1750 ppb within 0-5 minutes, 1750-1800 ppb within 0-5 minutes, 1800-1850 ppb within 0-5 minutes, 1850-1900 ppb within 0-5 minutes, 1900-1950 ppb within 0-5 minutes, or 1950-2000 ppb within 0-5 minutes.

In certain embodiments, the AOG is configured to release a total concentration of less than 10 ppb of ozone, 10 ppb of ozone, 20 ppb of ozone, 30 ppb of ozone, 40 ppb of ozone, 50 ppb of ozone, 60 ppb of ozone, 70 ppb of ozone, 80 ppb of ozone, 90 ppb of ozone, 100 ppb of ozone, or more than 100 ppb of ozone.

In some embodiments, along the direction of the flow of air, the particulate filter is positioned before the NCCO filter material, the NCCO filter material is positioned before the AOG, and the AOG is positioned before the fan unit.

In some embodiments, along the direction of the flow of air, the AOG is positioned before the particulate filter, the particulate filter is positioned before the NCCO filter material, and the NCCO filter material is positioned before the fan unit.

In some embodiments, the oxidant remover and the NCCO filter material are combined to form a single NCCO oxidant remover composition. In some embodiments, the oxidant remover is positioned on a surface of the NCCO filter opposing the air entrance. In some embodiments, the air purifier further comprises a pre-filter that is positioned to cover at least a portion of the air entrance and/or the air exit to filter air passing through the air entrance and/or the air exit.

In certain exemplary embodiment, a self-regenerating air purifier for air disinfection comprises a housing defining an enclosure and having an air entrance and nan air exit; a HEPA filter; a NCCO filter material configured to adsorb and decompose at least one gaseous pollutant; an ozone generator configured to generate ozone; an ozone remover material configured to remove ozone, comprising a catalyst composition comprising: a porous material having a plurality of nanopores and comprising one or more of silicon dioxide, aluminum oxide, and zeolite, and manganese oxides comprising manganese in an amount of about 0.1-50% by weight of the total catalyst composition; a fan unit configured to generate airflow from the air entrance to the air exit; a pre-filter positioned to cover at least a portion of the air entrance and/or the air exit to filter air passing through the air entrance and/or the air exit; wherein the HEPA filter, the NCCO filter material, the ozone generator, the ozone remover material and the fan unit are positioned within the enclosure such that a flow of air passes from the air entrance to the air exit through the HEPA filter and the NCCO filter material; wherein the ozone generator is configured to generate a concentration of ozone sufficient to disinfect at least 90% of bacteria/viruses.

In some embodiments, the concentration of ozone generated by the ozone generator is at least 40 ppb. In some embodiments, the flow of air first passes through the HEPA filter before passing through the NCCO filter material.

Example 3

Catalyst Composition

In this example, the oxidant remover material is called catalyst composition. In certain exemplary embodiments, the catalyst composition comprises a porous material having a plurality of nanopores and comprising one or more of silicon dioxide, aluminum oxide, and zeolite; and manganese oxides comprising manganese in an amount of about 0.1-50% by weight of the total catalyst composition.

In one exemplary embodiment, the zeolite comprises one or more aluminum oxides and silicon oxides. In some embodiments, the porous material is aluminum oxide. In some embodiments, the aluminum oxide comprises one or more amorphous aluminum oxide, crystalline aluminum oxide, activated aluminum oxide.

In certain exemplary embodiments, manganese oxides form one or more clusters on the porous material. In some embodiment, the manganese has an oxidation state of +2, +3, +4, +5 or +6.

In one exemplary embodiment, the manganese oxides are selected from the group consisting of MnO, MnO2, MnO3, Mn3 O4 and Mn2O3. In some embodiments, the manganese is equal to or less than 20% by weight of the total catalyst composition.

In certain embodiments, the manganese is 1-20% by weight of the total catalyst composition. In other exemplary embodiments, the manganese is 2-20% by weight, 3-20% by weight, 4-20% by weight, 5-20% by weight, 6-20% by weight, 7-20% by weight, 8-20% by weight, 9-20% by weight, 10-20% by weight of the total catalyst composition. In other exemplary embodiments, the manganese is 10.78% by weight of the total catalyst composition.

In certain embodiments, the zeolite comprises one or more aluminum oxides and silicon oxides. In some embodiments, the porous material is aluminum oxide. In some embodiments, the aluminum oxide comprises one or more amorphous aluminum oxide, crystalline aluminum oxide, and activated aluminum oxide.

In certain embodiments, the zeolite includes fibrous zeolites, wherein the fibrous zeolites include gonnardite, natrolite, mesolite, paranatrolite, scolecite, tetranatrolite, edingtonite, kalborsite, and thomsonite-series. In some embodiments, the zeolite includes the zeolites with chains of single connected 4-membered rings, including but not limited to analcime, leucite, pollucite, wairakite, laumontite, yugawaralite, goosecreekite, and montesommaite. In some embodiments, the zeolite includes the zeolites with chains of doubly connected 4-membered rings, including but not limited to harmotome, phillipsite-series, amicite, gismondine, garronite, gobbinsite, boggsite, merlinoite, mazzite-series, paulingite-series, and perlialite. In some embodiments, the zeolite includes the zeolites with chains of 6-membered rings, including but not limited to chabazite-series, herschelite, willhendersonite, SSZ-13, faujasite-series, Linde type X, Linde type Y, maricopaite, mordenite, offretite, wenkite, bellbergite, bikitaite, erionite-series, ferrierite, gmelinite, levyne-series, dachiardite-series, and epistilbite. In some embodiments, the zeolite includes the zeolites with chains of T10O20 tetrahedra (T=combined Si and Al), including but not limited to clinoptilolite, heulandite-series, barrerite, stellerite, stilbite-series, brewsterite-series. In some embodiments, the zeolite includes cowlesite, pentasil, tschernichite, and Linde type A framework.

In some embodiments, the catalyst compositions comprise manganese oxides and porous materials. The porous materials include granules silicon dioxides such as quartz, glass beads, silica gel or zeolites made up of aluminum oxides and silicon oxides with clear nano pore size (diameter) of 0.2-0.6 nm. In some embodiments, the nano pore size (diameter) of the nanopores is 0.2-0.4 nm. In some embodiments, the nano pore size is one or more of 0.1, 0.2, 0.3, 0.4, 0.5, or 0.6 nm.

In some embodiments, the catalyst composition is made by doping, ion exchange or deposition. Methods of doping, ion exchange, and deposition of manganese oxides on porous materials that are known in the art may be used.

In some embodiments, the silica gel is a clear pellet, having drying and moisture-proof properties. In some embodiments, the silica gel is a translucent white pellet and a liquid adsorbent. In some embodiments, the silica gel is translucent, has a micro-pored structure, or is a raw material used for the preparation of silica gel cat litter. In some embodiments, if additionally dried and screened, the silica gel forms macro-pored silica gel which is used as a drier, adsorbent and catalyst carrier. In some embodiments, the silica gel is in the form of a granule or a bead.

Silica gel has several advantages. In certain embodiments, silica gel provides good adhesion to manganese oxides. Silica gel is also inexpensive and mechanically robust.

In certain embodiments, the porous material is provided in the form of a granule. In some embodiments, the diameter of each granule is 3-5 mm. In some embodiments, the manganese oxides are added to the granule via doping, ion exchange or deposition.

In certain embodiments, the manganese oxides have a total band gap energy of 2.0 eV to 3.75 eV.

Figure 3A:
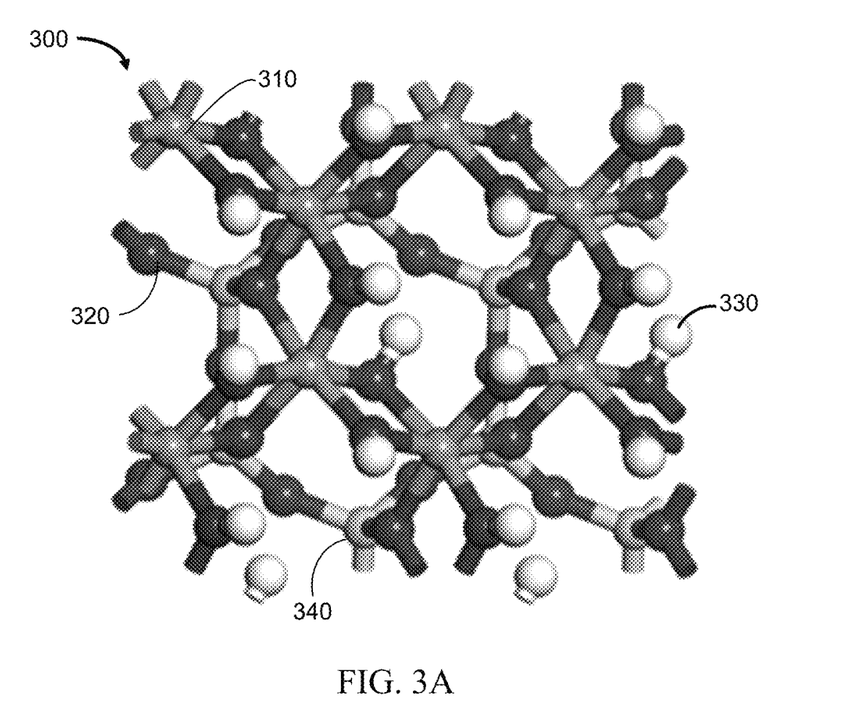
FIG. 3A is a ball-and-stick diagram which illustrates a top view of an example embodiment of manganese oxides doped on the silica materials.
Figure 3B:
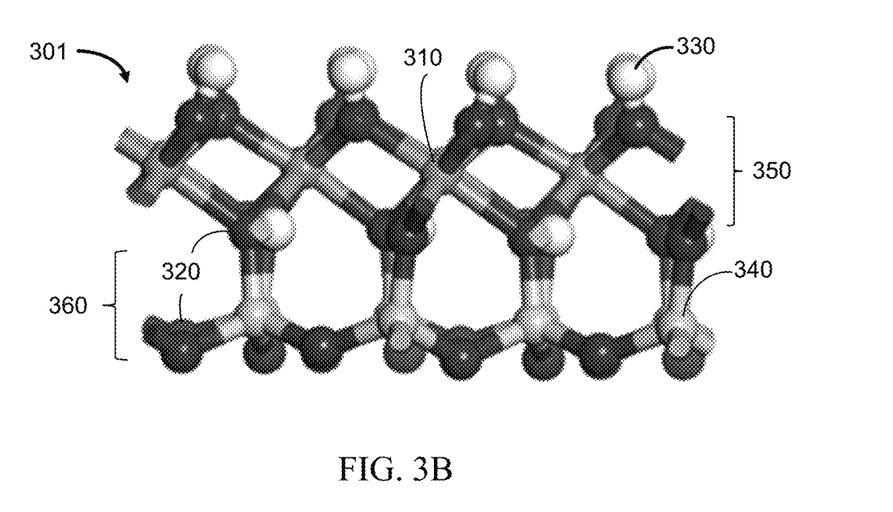
FIG. 3B is a ball-and-stick diagram which illustrates a side view of said example embodiment of manages oxides doped on the silica materials.

With reference to FIG. 3A and FIG. 3B, an example catalyst composition 300 may include a nano sheet 350 of manganese oxides formed on the silicon oxides. FIG. 3A is a ball-and-stick diagram that illustrates a top view of the catalyst composition 300. According to FIG. 3A, manganese 310 marked in purple and oxygen 320 marked in red are combined as manganese oxides and formed on a top layer of the catalyst composition 300. At the bottom layer, silicon 340 marked in yellow and oxygen 320 are combined as silicon oxides as the porous material according to an example embodiment. The silicon oxides serve as a platform on which the manganese oxides are formed. Hydrogen 330 molecules marked in white are bound to the oxygen 320 molecules.

FIG. 3B is a ball-and-stick diagram that illustrates a side view of the catalyst composition 300. According to FIG. 3B, a nano sheet layer 350 of the manganese oxides is formed on top of the bottom layer 360 of the silicon oxides. In some embodiments, the nano sheet layer 350 includes one or more layers of the manganese oxides on top of the porous materials.

Activation of Catalyst Composition

In one exemplary embodiment, the catalyst composition is oxidized by reactive oxygen species (ROS) directly generated by vacuum ultraviolet (VUV). In some embodiments, ROS oxidizes manganese oxides with the help of the catalyst composition to its higher oxidation state which reacts with formaldehyde to form carbon dioxide and water. In some embodiments, the high valent manganese ion in the catalyst returns to its original oxidation state after the oxidation.

In certain embodiments, ROS generated by VUV can oxidize the manganese doped porous material according to the reactions below, which reacts with formaldehyde to form carbon dioxide and water:

A) Mechanism of Ozone Scavenger $$O_3 + *MnOx \rightarrow O_2 + O*MnOx$$

$$O*MnOx + O_3 \rightarrow O_2 + O_2*MnOx$$

$$O_2*MnOx \rightarrow O_2 + *MnOx$$

B) Mechanism of Doped Manganese Oxide with ROS $$ROS + *MnOx \rightarrow O*MnOx$$

$$O*MnOx + H_2O + *MnOx \rightarrow 2(OH*MnOx)$$

$$OH*MnOx + ROS \rightarrow HO_2*MnOx$$

$$O*MnOx + ROS \rightarrow O_2*MnOx$$

In certain embodiments, species O*MnOx, O2*MnOx, OH*MnOx and HO2*MnOx can all react with formaldehyde to form carbon dioxide and water:

$$HCHO + *MnOx \rightarrow HCHO*MnOx$$

$$HCHO*MnOx + 2O*MnOx \rightarrow CO_2 + H_2O + 3*MnOx$$

$$HCHO*MnOx + O_2*MnOx \rightarrow CO_2 + H_2O + 2*MnOx$$

$$HCHO*MnOx + 2OH*MnOx + H + CO_2 + 2H_2O + 2*MnOx$$

$$HCHO*MnOx + HO_2*MnOx \rightarrow CO_2 + H_2O + H + + 2*MnOx$$

In certain embodiments, VUV with a wavelength 185 nm and 254 nm can generate many different types of ROS, including O., OH., HO2., O3 and H2O2, which can react with formaldehyde and re-generate the manganese doped silica material:

$$O_2 + h\nu \rightarrow 2O.$$

$$H_2O + h\nu \rightarrow H. + OH.$$

$$O + H_2O \rightarrow 2OH.$$

$$O. + O_2 \rightarrow O_3$$

$$OH. + OH. \rightarrow H_2O_2$$

$$H.+O_2 \rightarrow HO_2.$$

$$2HO_2. \rightarrow H_2O_2 + O_2$$

$$H_2O + hv \rightarrow H. + OH.$$

In certain embodiments, the manganese oxides formed on the porous materials serve as the photocatalyst. In some embodiments, the bandgap energy of manganese dioxide nano sheets is about 2.34 eV. A mesoporous structure containing Mn3O4 and Mn2O3 was found to have bandgap energies of 2.46 eV and 3.18 eV after calcination and uncalcined, respectively. One exemplary embodiment provides nano sheets of manganese oxides with multiple oxidation states and possessing a large number of band gaps over a large range (from 2.0 eV to 3.75 eV), which can absorb not only VUV but also visible light for photocatalytic oxidation of formaldehyde.

Preparation of Catalyst Composition

One exemplary embodiment provides a process for preparing the catalyst composition comprising: adding a porous material to a manganese salt solution to form a suspension; and calcinating the porous material, wherein at least one nano sheet of manganese oxides is formed on the porous material.

In certain exemplary embodiments, the process for preparing the catalyst composition is useful for manufacturing the catalyst composition in bulk. In some embodiments, the porous material is zeolite, aluminum oxide, or silica gel. In some embodiments, the zeolite is aluminum zeolite, analcime, chabazite, clinoptilolite, heulandite, natrolite, phillipsite, stilbite, or natrolite.

In certain exemplary embodiments, the aluminum zeolite is 50-150 g by weight. In some embodiments, the aluminum zeolite is approximately 110 g by weight.

In certain embodiments, the process may further comprise washing the porous material with water and/or acid before adding the porous material to the manganese salt solution. In certain embodiments, the process may further comprise during the porous material on a glass tray after washing the porous material and before adding the porous material to the manganese salt solution.

In certain exemplary embodiments, the step of drying the porous material is performed at room temperature, 25-50° C., 50-75° C., 75-100° C., 100-125° C., 125-150° C., 150-175° C., 175-200° C. or higher than 200° C. In certain exemplary embodiments, the step of drying the porous material is performed at 25-30° C., 30-35° C., 35-40° C., 40-45° C., 45-50° C., 50-55° C., 55-60° C., 60-65° C., 65-70° C., 70-75° C., 75-80° C., 80-85° C., 85-90° C., 90-95° C., 95-100° C., 100-105° C., 105-110° C., 110-115° C., 115-120° C., 120-125° C., 125-130° C., 130-135° C., 135-140° C., 140-145° C., 145-150° C., 150-155° C., 155-160° C., 160-165° C., 165-170° C., 170-175° C., 175-180° C., 180-185° C., 185-190° C., 190-195° C. or 195-200° C. In some embodiments, the step of drying the porous material is performed at approximately 130° C. In some embodiments, the step of drying the porous material is performed for about 1.5 hours. In some embodiments, the step of drying the porous material is performed overnight.

In certain exemplary embodiments, the manganese salt is manganese (II) acetate, manganese sulfate, manganese (III) acetate, manganese (III) acetylacetonate, manganese chloride, or manganese (II) nitrate.

In certain exemplary embodiments, the process further comprises weighing the dried porous material and the manganese salt after adding the porous material. In some embodiments, the weight of the manganese salt is 0.48 times the weight of the dried porous material.

In certain exemplary embodiments, the process further comprises stirring the suspension after adding the porous material to the manganese salt solution. In some embodiments, the step of stirring the suspension is performed for less than 1 hour. In some embodiments, the step of stirring the suspension is performed for at least 1 hour. In some embodiments, the step of stirring the suspension is performed for 1-20 hours, 1-15 hours, 1-10 hours or 1-5 hours. In some embodiments, the step of stirring the suspension is performed for 5-20 hours, 5-15 hours or 5-10 hours. In some embodiments, the step of stirring the suspension is performed for 10-20 hours or 10-15 hours. In some embodiments, the step of stirring the suspension is performed for approximately 15 hours. In some embodiments, the step of stirring the suspension is performed overnight.

In certain exemplary embodiments, the step of stirring the suspension is replaced by the step of letting the suspension stand In certain exemplary embodiments, the process further comprises filtering the porous material after adding the porous material to the manganese salt solution. In some embodiments, the process further comprises drying the filtered porous material. In some embodiments, the step of filtering is performed using a soup filter bag.

In certain exemplary embodiments, the step of calcinating the porous material is performed at 100-110° C., 110-120° C., 120-130° C., 130-140° C., 140-150° C., 150-160° C., 160-170° C., 170-180° C., 180-190° C., 190-200° C., 200-210° C.° C., 210-220° C.° C., 220-230° C., 230-240° C., 240-250° C., 250-260° C., 260-270° C., 270-280° C., 280-290° C., 290-300° C., 310-320° C., 320-330° C., 330-340° C., 340-350° C., 350-360° C., 360-370° C., 370-380° C., 380-390° C., 390-400° C., 410-420° C., 420-430° C., 430-440° C., 440-450° C., 450-460° C., 460-470° C., 470-480° C., 480-490° C. or 490-500° C. In certain exemplary embodiments, the step of calcinating the porous material is performed at 100-120° C., 120-140° C., 140-160° C., 160-180° C., 180-200° C., 200-220° C., 220-240° C., 240-260° C., 260-280° C., 280-300° C., 300-320° C., 320-340° C., 340-360° C., 360-380° C., 380-400° C., 400-420° C., 420-440° C., 440-460° C., 460-480° C. or 480-500° C. In some embodiments, the step of calcinating the porous material is performed at 100-150° C., 150-200° C., 200-250° C., 250-300° C., 300-350° C., 350-400° C., 400-450° C. or 450-500° C. In some embodiments, the step of calcinating the porous material is performed at approximately 100° C., 200° C., 300° C., 400° C. or 500° C. In some embodiments, the step of calcinating the porous material is performed at 500° C. or more. In some embodiments, the step of calcinating the porous material is performed at less than 100° C.

In certain exemplary embodiments, the process further comprises cooling down the porous materials to room temperature after calcinating the porous material.

Figure 4:
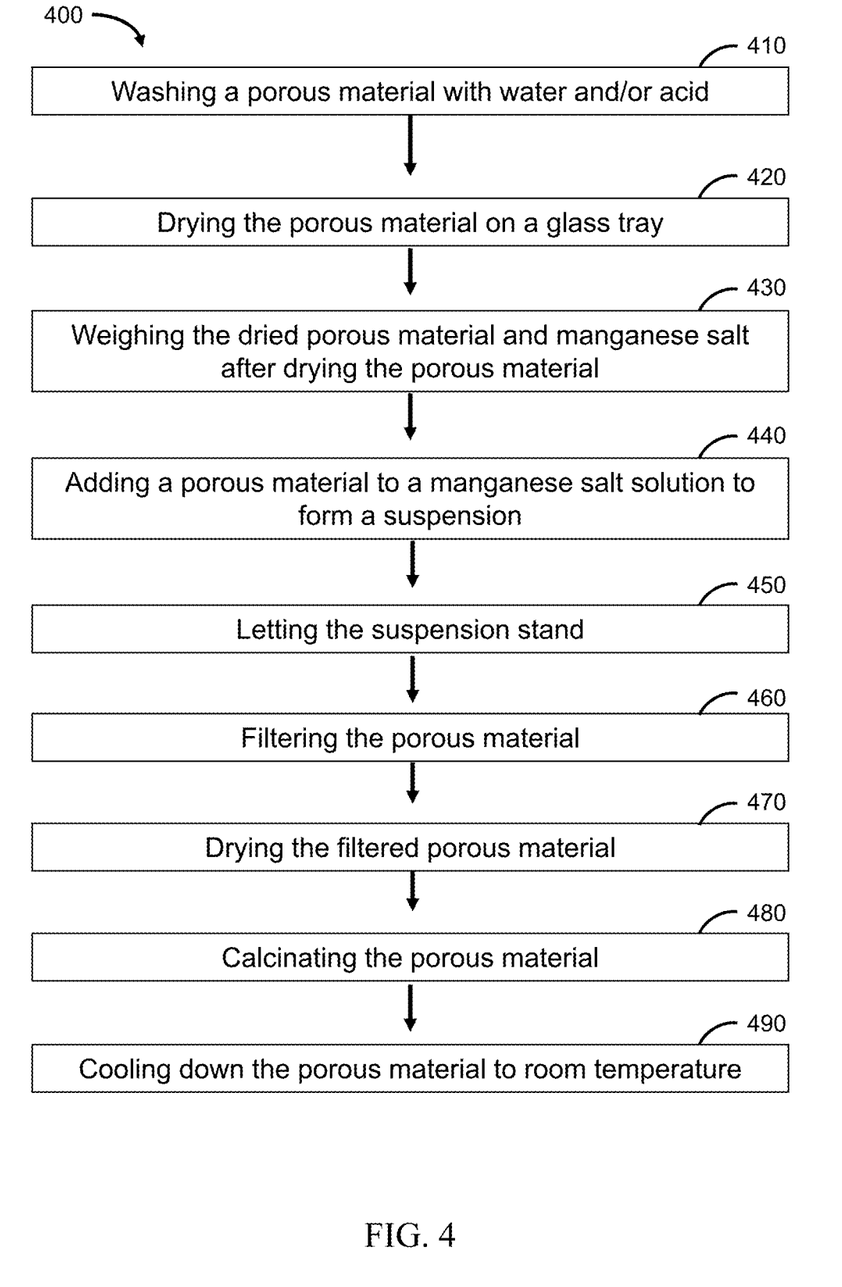
FIG. 4 is a flowchart which illustrates a method for preparing a catalyst composition in accordance with an example embodiment.

In the embodiment of FIG. 4, a method 400 for preparing a catalyst composition is illustrated. The steps are in sequential order, starting from Block 410 to 390.

The first step Block 410 states washing a porous material with water and/or acid. By way of example, the porous material is aluminum zeolite, aluminum oxide, or silica gel. In some embodiments, the porous material is approximately 10 g, 20 g, 30 g, 40 g, 50 g, 60 g, 70 g, 80 g, 90 g, 100 g, 110 g, 120 g, 130 g, 140 g, 150 g, 160 g, 170 g, 180 g, 190 g or 200 g by weight. The acid includes but is not limited to oxalic acid, sulphuric acid, tridecyl benzene sulphonic acid and hydrochloric acid, The next step Block 420 states drying the porous material on a glass tray. In some embodiment, the step of drying the porous material on the glass tray is performed at 130° C. for 1.5 hours.

Block 430 states weighing the dried porous material and manganese salt after drying the porous material. In some embodiments, the weight of the manganese salt is 0.48 times the weight of the dried porous material. In some embodiments, the weight of the manganese salt is 0.4-0.5 times the weight of the dried porous material. In some embodiments, the weight of the manganese salt is 0.3-0.6 times the weight of the dried porous material. In some embodiments, the weight of the manganese salt is 0.2-0.8 times the weight of the dried porous material. In some embodiments, the weight of the manganese salt is 0.1-1 times the weight of the dried porous material.

Block 440 states adding a porous material to a manganese salt solution to form a suspension. In some embodiments, the manganese salt is manganese (II) acetate.

Block 450 states letting the suspension stand. In some embodiments, the step of letting the suspension stand is performed for 1-24 hours, 1-20 hours, 2-20 hours, 3-20 hours, 4-20 hours, 5-20 hours, 6-20 hours, 7-20 hours, 8-20 hours, 9-20 hours, 10-20 hours, 11-20 hours, 12-20 hours, 13-20 hours, 14-20 hours, 15-20 hours, 1-15 hours, 2-15 hours, 3-15 hours, 4-15 hours, 5-15 hours, 6-15 hours, 7-15 hours, 8-15 hours, 9-15 hours, 10-15 hours, 11-15 hours, 12-15 hours, 13-15 hours, 14-15 hours, or approximately 15 hours.

Block 460 states filtering the porous material. In some embodiments, the step of filtering the porous material is performed using a soup filter bag.

Block 470 states drying the filtered porous material. In some embodiments, the step of drying the filtered porous material is skipped. In other embodiments, it is included.

Block 480 states calcinating the porous material. In some embodiments, the step of calcinating the porous material is performed at approximately 300° C. In some embodiments, the step of calcinating the porous material is performed at 100-500° C., 200-400° C., 250-350° C., 275-325° C., below 500° C., below 400° C., or below 300° C.

Block 490 states cooling down the porous material to room temperature.

One exemplary embodiment provides a method of synthesizing manganese doped granular silica mineral, comprising the steps of: (a) washing the granular silica mineral with diluted water three times followed by 2M sulfuric acid; (b) preparing a solution of manages acetate (1-20%) mass ratio); (c) transferring the granular silica mineral to the manganese acetate solution and stirring for 5 min; (d) filtering and drying the granular silica mineral under ambient conditions; (e) calcinating the granular silica mineral at 250° C. for 2 hours; and cooling it down to room temperature to obtain the manganese doped granular silica mineral.

Another exemplary embodiment provides a method of synthesizing manganese doped granular silica mineral, comprising the steps of: (a) weighing approximately 110 g Al zeolite in a 250 ml beaker; (b) drying the Al zeolite on a glass tray in 130° C. for 1.5 hours; (c) letting the Al zeolite cool down to reasonable temperature and weighing the Al zeolite; (d) weighing (0.48*zeolite dry mass) g Mn(CH3COO)2.4H2O in a 1000 mL beaker; (e) measuring 480 mL distilled H2O in a 2000 ml measuring cylinder, pouring into the 1000 mL beaker and stirring with glass rod until all Mn(CH3COO)2.4H2O dissolves; (f) pouring Al zeolite into the solution and letting the mixture stand for 15 hours; (g) filtering the solution through soup filter bag; (h) pouring the filtered Al zeolite into a glass tray and roughly spreading the Al zeolite evenly on the tray; (i) calcinating the Al zeolite in a furnace at 300° C. for 2 hours; (j) letting the Al zeolite cool to room temperature, storing the zeolite in resealable plastic bags and labeling batch number, reference number(s) and conditions on the bag.

NUMBERED EMBODIMENTS

Set 1

1. An air purifier, comprising:
    a housing defining an enclosure and having an air entrance and an air exit;
    a particulate filter;
    a nano-confined catalytic oxidation (NCCO) filter material configured to adsorb and decompose at least one gaseous pollutant;
    an active oxygen generator (AOG) configured to generate at least one oxidant;
    an oxidant remover material configured to remove at least one oxidant; and
    a fan unit configured to generate airflow from the air entrance to the air exit;
    wherein the particulate filter, the NCCO filter material, the AOG, the oxidant remover material and the fan unit are positioned within the enclosure such that during operation, a flow of air passes from the air entrance to the air exit through the particulate filter and the NCCO filter material along a direction of the flow of air.

2. The air purifier of embodiment 1, wherein the catalyst layer further comprises a nano-confined catalytic oxidation (NCCO) filter material.

3. The air purifier of embodiment 1, wherein the AOG is an ozone generator and the at least one oxidant is ozone.

4. The air purifier of embodiment 1 or embodiment 3, wherein the oxidant remover material is an ozone remover material.

5. The air purifier of embodiment 4, wherein the ozone remover material has a thickness of about 5-20 mm.

6. The air purifier of any one of embodiments 1-5, wherein the particulate filter is a high-efficiency particulate air (HEPA) filter.

7 The air purifier of embodiment 4, wherein the ozone remover material comprises a catalyst composition comprising:
    a porous material having a plurality of nanopores and comprising one or more of silicon dioxide, aluminium oxide, and zeolite; and
    manganese oxides comprising manganese in an amount of about 0.1-50% by weight of the total catalyst composition.

8. The air purifier of embodiment 7, wherein the manganese oxides form one or more clusters on the porous material.

9. The air purifier of embodiment 7 or embodiment 8, wherein the manganese has an oxidation state of +2, +3, +4, +5 or +6.

10. The air purifier of any one of embodiment 7 or embodiment 8, wherein the manganese oxides are selected from the group consisting of $MnO$, $MnO_2$, $MnO_3$, $Mn_3O_4$ and $Mn_2O_3$.

11. The air purifier of any one of embodiments 7-10, wherein the manganese is equal to or less than 20% by weight of the total catalyst composition.

12. The air purifier of embodiment 11, wherein the manganese is 1-20% by weight of the total catalyst composition.

13. The air purifier of embodiment 12, wherein the manganese is 4-20% by weight of the total catalyst composition.

14. The air purifier of any one of embodiment 7, wherein the zeolite comprises one or more of aluminum oxides and silicon oxides.
15. The air purifier of any one of embodiments 7-14, wherein the porous material is aluminium oxide.
16. The air purifier of embodiment 15, wherein the aluminium oxide comprises one or more of amorphous aluminium oxide, crystalline aluminium oxide, activated aluminium oxide.
17. The air purifier of any one of embodiments 7-16 wherein the diameter of the nanopores is 0.6 nm-20 angstrom.
18. The air purifier of embodiment 17, wherein the diameter of the nanopores is 0.2-0.4 nm.
19. The air purifier of any one of embodiments 7-18, wherein the porous material is provided in a form of a granule.
20. The air purifier of embodiment 19, wherein the diameter of each granule is 3-5 mm.
21. The air purifier of embodiment 7, wherein the manganese oxides are added to the granules via doping, ion exchange or deposition.
22. The air purifier of any one of embodiments 7-21, wherein the manganese oxides have total bandgap energy of 2.0 eV to 3.75 eV.
23. The air purifier of any one of the preceding embodiments, wherein the AOG is configured to generate a concentration of ozone sufficient to disinfect at least 90% of bacteria/viruses.
24. The air purifier of embodiment 23, wherein the AOG is configured to generate an ozone release rate of at least 10-2000 ppb within 0-5 minutes.
25. The air purifier of embodiment 24, wherein the ozone release rate is at least 40 ppb over 1 minute.
26. The air purifier of embodiment 24, wherein the AOG is configured to release a total concentration of at least 40 ppb of ozone.
27. The air purifier of any one of embodiments 1-26, wherein the oxidant remover material and the NCCO filter material are combined to form a single NCCO oxidant remover composition.
28. The air purifier of any one of embodiments 1-26, wherein the oxidant remover material is positioned on a surface of the NCCO filter material opposing the air entrance.
29. The air purifier of any one of embodiments 1-28, wherein along the direction of the flow of air, the AOG is positioned before the particulate filter, the particulate filter is positioned before the NCCO filter material, and the NCCO filter material is positioned before the fan unit.
30. The air purifier of any one of embodiments 1-28, wherein along the direction of the flow of air, the particulate filter is positioned before the NCCO filter material, the NCCO filter material is positioned before the AOG, and the AOG is positioned before the fan unit.
31. The air purifier of any one of the preceding embodiments, further comprising a pre-filter that is positioned to cover at least a portion of the air entrance and/or the air exit to filter air passing through the air entrance and/or the air exit.
32. A self-regenerating air purifier for air disinfection, comprising:
    a housing defining an enclosure and having an air entrance and an air exit;
    a high-efficiency particulate air (HEPA) filter;
    a nano-confined catalytic oxidation (NCCO) filter material configured to adsorb and decompose at least one gaseous pollutant;
    an ozone generator configured to generate ozone;
    an ozone remover material configured to remove ozone, comprising a catalyst composition comprising:
        a porous material having a plurality of nanopores and comprising one or more of silicon dioxide, aluminum oxide, and zeolite, and manganese oxides comprising manganese in an amount of about 0.1-50% by weight of the total catalyst composition;
    a fan unit configured to generate airflow from the air entrance to the air exit;
    a pre-filter positioned to cover at least a portion of the air entrance and/or the air exit to filter air passing through the air entrance and/or the air exit;
    wherein the HEPA filter, the NCCO filter material, the ozone generator, the ozone remover material and the fan unit are positioned within the enclosure such that a flow of air passes from the air entrance to the air exit through the HEPA filter and the NCCO filter material;
    wherein the ozone generator is configured to generate a concentration of ozone sufficient to disinfect at least 90% of bacteria/viruses.
33. The self-regenerating air purifier for air disinfection of embodiment 32, wherein the concentration of ozone generated by the ozone generator is at least 40 ppb.
34. The self-regenerating air purifier for air disinfection of embodiment 32, wherein the flow of air first passes through the HEPA filter before passing through the NCCO filter material.

Set 2
1. A catalyst composition comprising:
   a porous material having a plurality of nanopores; and
   manganese oxides comprising manganese in an amount of about 0.1-50% by weight of the total catalyst composition.
2. A catalyst composition comprising:
   a porous material having a plurality of nanopores and comprising one or more of silicon dioxide, aluminum oxide and zeolite; and
   manganese oxides comprising manganese in an amount of about 0.1-50% by weight of the total catalyst composition,
   wherein a nano sheet of the manganese oxides is formed on the porous material.
3. The catalyst composition of embodiment 1 or 2, wherein the manganese oxides form one or more clusters on the porous material.
4. The catalyst composition of any one of embodiments 1-3, wherein the manganese oxides are selected from the group consisting of MnO, MnO2, MnO3, Mn3O4 and Mn2O3.
5. The catalyst composition of any one of embodiments 1-4, wherein the porous material is aluminum oxide.
6. The catalyst composition of embodiment 5, wherein the aluminum oxide comprises one or more amorphous aluminum oxide, crystalline aluminum oxide, activated aluminum oxide.
7. A process for preparing the catalyst composition of any one of embodiments 1-6, comprising:
   adding a porous material to a manganese salt solution to form a suspension; and calcinating the porous material;
   wherein at least one nano sheet of manganese oxides is formed on the porous material.
8. The process for preparing the catalyst composition of any one of embodiments 1-6, comprising:
   washing the porous material with water and/or acid;
   adding a porous material to a manganese salt solution to form a suspension; and
   calcinating the porous material;
   wherein at least one nano sheet of manganese oxides is formed on the porous material.

9. The process for preparing the catalyst composition of any one of embodiments 1-6, comprising:
washing the porous material with water and/or acid;
drying the porous material on a glass tray;
adding a porous material to a manganese salt solution to form a suspension; and calcinating the porous material;
wherein at least one nano sheet of manganese oxides is formed on the porous material.

10. The process for preparing the catalyst composition of any one of embodiments 1-6, comprising:
washing the porous material with water and/or acid;
drying the porous material on a glass tray;
weighing the dried porous material and the manganese salt after drying the porous material;
adding a porous material to a manganese salt solution to form a suspension; and
calcinating the porous material;
wherein at least one nano sheet of manganese oxides is formed on the porous material.

11. The process for preparing the catalyst composition of embodiment 10, wherein the weight of the manganese salt is 0.48 times the weight of the dried porous material.

12. The process for preparing the catalyst composition of any one of embodiments 1-6, comprising:
washing the porous material with water and/or acid;
drying the porous material on a glass tray;
weighing the dried porous material and the manganese salt after drying the porous material;
adding a porous material to a manganese salt solution to form a suspension; stirring the suspension after adding the porous material to the manganese salt solution; and
calcinating the porous material;
wherein at least one nano sheet of manganese oxides is formed on the porous material.

13. The process for preparing the catalyst composition of any one of embodiments 1-6, comprising:
washing the porous material with water and/or acid;
drying the porous material on a glass tray;
weighing the dried porous material and the manganese salt after drying the porous material;
adding a porous material to a manganese salt solution to form a suspension; stirring the suspension after adding the porous material to the manganese salt solution;
filtering the porous material;
calcinating the porous material; and
cooling down the porous material to room temperature after calcinating the porous material
wherein at least one nano sheet of manganese oxides is formed on the porous material.

14. The process for preparing the catalyst composition of any one of the preceding embodiments, wherein the porous material is zeolite, aluminum oxide, or silica gel.

15. The process for preparing the catalyst composition of embodiment 14, wherein the zeolite is aluminum zeolite, analcime, chabazite, clinoptilolite, heulandite, natrolite, phillipsite, stilbite, or natrolite.

16. The process for preparing the catalyst composition of embodiments 9-15, wherein the step of drying the porous material is performed at room temperature, 25-50° C., 50-75° C., 75-100° C., 100-125° C., 125-150° C., 150-175° C., or 175-200° C.

17. The process for preparing the catalyst composition of embodiment 16, wherein the step of drying the porous material is performed for 1.5 hours.

18. The process for preparing the catalyst composition of any one of embodiments 7-17, wherein the manganese salt is manganese (II) acetate, manganese sulfate, manganese (III) acetate, manganese (III) acetylacetonate, manganese chloride, or manganese (II) nitrate.

19. The process for preparing the catalyst composition of any one of embodiments 7-18, wherein the step of calcinating the porous material is performed at 200-220° C., 220-240° C., 240-260° C., 260-280° C., 280-300° C., 300-320° C., 320-340° C., 340-360° C., 360-380° C., or 380-400° C.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein. Any modifications, equivalent replacements and improvements made within the technical conception of the present invention shall fall within the scope of the present invention.

For example, in certain examples, the zeolite may be used as the NCCO filter material. However, in some other embodiments, other suitable porous materials such as silicon dioxide, aluminium oxide may be used.

For example, in certain embodiments, a pre-filter is included in the air purifier. However, in some other embodiments, one or more different pre-filters may be provided. However, in some other embodiments, the air purifier may not include pre-filters.

For example, in certain embodiments, a particulate filter is included in the air purifier. However, in some other embodiments, one or more different particulate filters may be provided. However, in some other embodiments, the air purifier may not include particulate filters.

For example, in certain examples, the catalyst layer may comprise the NCCO filter material and oxidant remover material. However in some other embodiments, the NCCO filter material and oxidant remover material may form from the same catalyst composition. In other words, the catalyst composition may functionally serve as both the NCCO filter material to adsorb and decompose at least one gaseous pollutant as well as the oxidant remover material to remove at least one excessive oxidant.

For example, a power supply unit is needed to run the air purifier but is not described in detail as it is clear to one skilled in the art that electrical power is needed for the operation of the device. The power supply unit may be in electrical connection with at least the fan unit and the AOG. The device may include processor/control unit, memory unit, at least one rechargeable or non-rechargeable battery pack, battery charger port, power switch, and power management electronic circuit. The device may directly obtain the power from direct current (DC) source. Control unit may be provided to give command to the air purifier according to pre-defined instructions. Display unit may be provided for user interface. The display unit may be incorporated with a touch screen panel; therefore, it can receive command from the touch of user fingers.

What is claimed is:
1. An air purifier, comprising:
a housing defining an enclosure and having an air entrance and an air exit;
at least one particulate filter;
an active oxygen generator (AOG) configured to generate at least one oxidant;
a catalyst layer comprising an oxidant remover material; and
a fan unit configured to generate airflow from the air entrance to the air exit;
wherein the particulate filter, the catalyst layer, the AOG and the fan unit are positioned within the enclosure such that during operation, a flow of air passes from the air entrance to the air exit through the particulate filter and the catalyst layer along a direction of the flow of air;

wherein the oxidant remover material is an ozone remover material;

wherein the ozone remover material comprises a catalyst composition comprising:

a porous material having a plurality of nanopores and comprising one or more of silicon dioxide, aluminium oxide, and zeolite; and manganese oxides comprising manganese in an amount of 1-20% by weight of the total catalyst composition;

wherein the zeolite are aluminosilicate minerals.

2. The air purifier of claim 1, wherein the catalyst layer further comprises a nano-confined catalytic oxidation (NCCO) filter material.

3. The air purifier of claim 2, wherein the oxidant remover material and the NCCO filter material are combined to form a single NCCO oxidant remover composition.

4. The air purifier of claim 2, wherein the oxidant remover material is positioned on a surface of the NCCO filter material opposing the air entrance.

5. The air purifier of claim 2, wherein along the direction of the flow of air, the AOG is positioned before the particulate filter, the particulate filter is positioned before the NCCO filter material, and the NCCO filter material is positioned before the fan unit.

6. The air purifier of claim 2, wherein along the direction of the flow of air, the particulate filter is positioned before the NCCO filter material, the NCCO filter material is positioned before the AOG, and the AOG is positioned before the fan unit.

7. The air purifier of claim 1, further comprising a pre-filter that is positioned to cover at least a portion of the air entrance and/or the air exit to filter air passing through the air entrance and/or the air exit.

8. The air purifier of claim 1, wherein the ozone remover material has a thickness of about 5-20 mm.

9. The air purifier of claim 1, wherein the particulate filter is a high-efficiency particulate air (HEPA) filter.

10. The air purifier of claim 1, wherein the manganese oxides form one or more clusters on the porous material.

11. The air purifier of claim 1, wherein the manganese has an oxidation state of +2, +3, +4, +5 or +6.

12. The air purifier of claim 1, wherein the manganese oxides are selected from the group consisting of MnO, MnO2, MnO3, Mn3O4 and Mn2O3.

13. The air purifier of claim 1, wherein the manganese is equal to or less than 20% by weight of the total catalyst composition.

14. The air purifier of claim 1, wherein the porous material is aluminium oxide.

15. The air purifier of claim 14, wherein the aluminium oxide comprises one or more of amorphous aluminium oxide, crystalline aluminium oxide, activated aluminium oxide.

16. The air purifier of claim 1, wherein the diameter of the nanopores is 0.6 nm-20 angstrom.

17. The air purifier of claim 1, wherein the porous material is provided in a form of granules.

18. The air purifier of claim 17, wherein the diameter of each granule is 3-5 mm.

19. The air purifier of claim 17, wherein the manganese oxides are added to the granules via doping, ion exchange or deposition.

20. The air purifier of claim 1, wherein the manganese oxides have total bandgap energy of 2.0 eV to 3.75 eV.

21. The air purifier of claim 1, wherein the AOG is configured to generate an ozone release rate of at least 10-2000 ppb within 0-5 minutes.

22. The air purifier of claim 21, wherein the ozone release rate is at least 40 ppb over 1 minute.

23. The air purifier of claim 21, wherein the AOG is configured to release a total concentration of at least 40 ppb of ozone.

24. The air purifier of claim 1, wherein the particulate filter is a high-efficiency particulate air (HEPA) filter;

the catalyst layer further comprises a nano-confined catalytic oxidation (NCCO) filter material configured to adsorb and decompose at least one gaseous pollutant;

the AOG is an ozone generator configured to generate ozone;

the oxidant remover material comprises a catalyst composition comprising:

a porous material having a plurality of nanopores and comprising one or more of silicon dioxide, aluminum oxide, and zeolite, and manganese oxides comprising manganese in an amount of about 0.1-50% by weight of the total catalyst composition;

the air purifier further comprises a pre-filter positioned to cover at least a portion of the air entrance and/or the air exit to filter air passing through the air entrance and/or the air exit;

the HEPA filter, the NCCO filter material, the ozone generator, the ozone remover material and the fan unit are positioned within the enclosure such that a flow of air passes from the air entrance to the air exit through the HEPA filter and the NCCO filter material; and the ozone generator is configured to generate a concentration of ozone sufficient to disinfect at least 90% of bacteria/viruses.

25. The air purifier of claim 24, wherein the concentration of ozone generated by the ozone generator is at least 40 ppb.

26. The air purifier of claim 24, wherein the flow of air first passes through the HEPA filter before passing through the NCCO filter material.

27. The air purifier of claim 1, wherein the AOG is an ozone generator and the at least one oxidant is ozone.

28. The air purifier of claim 1, wherein the manganese is 4-20% by weight of the total catalyst composition.

29. The air purifier of claim 1, wherein the diameter of the nanopores is 0.2-0.4 nm.

30. The air purifier of claim 1, wherein the catalyst composition comprises one or more layers of nano sheet of the manganese oxides on top of the porous material.

* * * * *